United States Patent [19]

Orikasa et al.

[11] Patent Number: 5,692,898

[45] Date of Patent: Dec. 2, 1997

[54] ORTHODONTIC BRACKET

[75] Inventors: Masaaki Orikasa; Kozo Kawaguchi, both of Fukushima-ken, Japan

[73] Assignee: GAC International, Inc., Central Islip, N.Y.

[21] Appl. No.: 549,355

[22] Filed: Oct. 27, 1995

Related U.S. Application Data

[62] Division of Ser. No. 293,997, Aug. 22, 1994, Pat. No. 5,595,484.

[30] Foreign Application Priority Data

Apr. 13, 1994 [JP] Japan ................... 6-097866

[51] Int. Cl.$^6$ ............................................. A61C 3/00
[52] U.S. Cl. ....................................... 433/8; 433/9
[58] Field of Search ........................... 433/8, 9, 10, 11, 433/12, 13, 14, 15, 16, 17

[56] References Cited

U.S. PATENT DOCUMENTS

| | | | |
|---|---|---|---|
| 2,908,974 | 10/1959 | Stifter | 32/14 |
| 3,469,314 | 9/1969 | Pearlman | 32/14 |
| 3,765,091 | 10/1973 | Northcutt | 32/14 A |
| 3,775,850 | 12/1973 | Northcutt | 32/14 A |
| 3,922,787 | 12/1975 | Fischer et al. | 433/15 |
| 3,930,311 | 1/1976 | Andrews | 32/14 A |
| 3,964,165 | 6/1976 | Stahl | 32/14 A |
| 4,050,156 | 9/1977 | Chasanoff et al. | 32/2 |
| 4,107,844 | 8/1978 | Kurz | 32/14 A |
| 4,186,488 | 2/1980 | Wallshein | 433/8 |
| 4,249,897 | 2/1981 | Anderson | 433/8 |
| 4,299,569 | 11/1981 | Frantz | 433/8 |
| 4,302,532 | 11/1981 | Wallshein | 433/8 |
| 4,353,692 | 10/1982 | Karrakussoglu | 433/16 |
| 4,674,978 | 6/1987 | Acevedo | 433/8 |
| 4,717,341 | 1/1988 | Goldberg et al. | 433/9 |
| 4,850,865 | 7/1989 | Napolitano | 433/8 |
| 4,894,012 | 1/1990 | Goldberg et al. | 433/215 |
| 4,927,361 | 5/1990 | Smith et al. | 433/9 |
| 4,948,366 | 8/1990 | Horn et al. | 433/9 |
| 5,078,596 | 1/1992 | Carberry et al. | 433/8 |
| 5,108,285 | 4/1992 | Tuneberg | 433/9 |
| 5,141,436 | 8/1992 | Orlowski et al. | 433/226 |
| 5,197,873 | 3/1993 | Wong et al. | 433/9 |
| 5,254,002 | 10/1993 | Reher et al. | 433/8 |
| 5,302,121 | 4/1994 | Gagin | 433/10 |
| 5,318,440 | 6/1994 | Adam et al. | 433/8 |
| 5,358,402 | 10/1994 | Reed et al. | 433/8 |
| 5,380,196 | 1/1995 | Kelly et al. | 433/8 |

FOREIGN PATENT DOCUMENTS

| | | | |
|---|---|---|---|
| 0 316 086 | 5/1989 | European Pat. Off. | A61K 6/08 |
| 0 476 789 | 3/1992 | European Pat. Off. | A61K 6/083 |
| 41 35 434 | 4/1993 | Germany | A61C 7/12 |
| 43 43 275 | 6/1994 | Germany | A61C 7/12 |

OTHER PUBLICATIONS

*Journal of Clinical Orthodontics*, Mar. 1989; Tella Tech Advertisement.
*Journal of Clinical Orthodontics*, Jan. 1989; Product News Column.
*Journal of Clinical Orthodontics*, Sep. 1986; MIRAGE bracket advertisement.
*American Journal of Orthodontics*, vol. 89, No. 6 (Jun. 1986); American Orthodontics Advertisement.
*American Journal of Orthodontics and Dentofacial Orthopedics*, vol. 95, No. 5 (May 1989); SILKON Bracket Advertisement.
*Journal of Clinical Orthodontics*, Sep. 1990; Ormco Advertisement.

*Primary Examiner*—Nicholas D. Lucchesi
*Attorney, Agent, or Firm*—Kenyon & Kenyon

[57] ABSTRACT

An orthodontic bracket is provided including a plastic bracket body and a metal reinforcement member partly embedded in the bracket body. The bracket body includes a slot extending substantially along a mesial-distal axis of the bracket body for receiving an arch wire. The reinforcement member includes a holding notch having a width that is smaller than that of the slot of the bracket body. The holding notch is positioned inside the slot and spaced-apart from the slot surfaces to form an arch wire holding mechanism for engaging the arch wire and to substantially avoid contact between the arch wire and the surfaces of the slot.

12 Claims, 8 Drawing Sheets

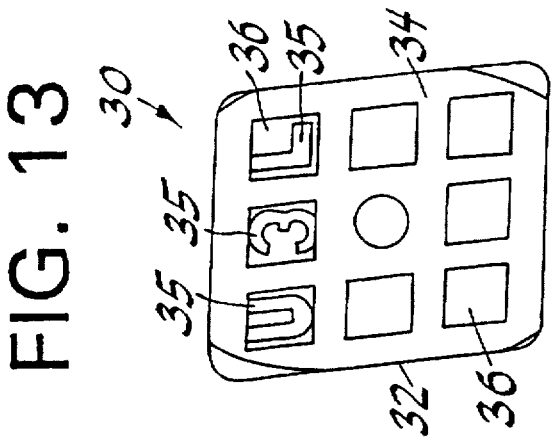
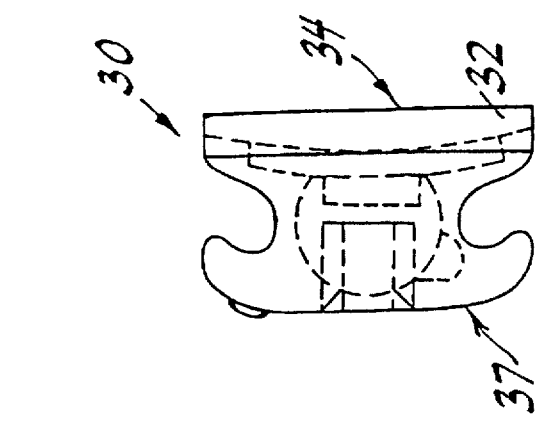
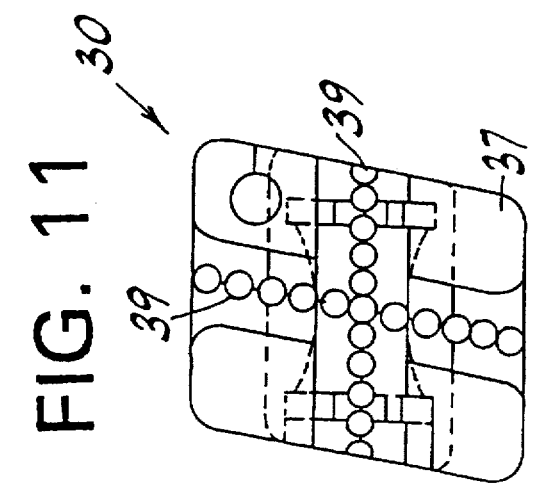
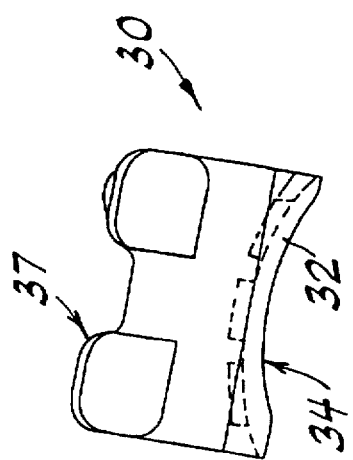

ORTHODONTIC BRACKET

This application is a division of application Ser. No. 08/293,997, filed on Aug. 22, 1994 now U.S. Pat. No. 5,595,484.

TECHNICAL FIELD OF THE INVENTION

The present invention relates generally to orthodontic brackets and, particularly, to plastic orthodontic brackets having a metal reinforcement member therein.

BACKGROUND OF THE INVENTION

Transparent or semi-transparent ceramic orthodontic brackets are more aesthetically appealing than conventional metal brackets. However, one problem with ceramic brackets is that they are generally harder than tooth enamel, which may create tooth wear problems during occlusion.

Transparent or semi-transparent plastic brackets have problems of cracking or deforming when torque is applied to the bracket by rectangular arch wires. Plastic brackets are also generally easily discolored by substances like coffee. However, resins with low absorption coefficients have been developed for use in plastic brackets that inhibit discoloring by substances like coffee.

Plastic brackets having a reinforcement member therein have also been developed as disclosed in U.S. Pat. Nos. 3,930,311; 4,299,569; and 4,302,532. The durability of a plastic bracket can be increased by inserting a metal reinforcement member therein to inhibit cracking or deformation of the bracket.

Known metal reinforcement members for reinforced plastic brackets disclosed in U.S. Pat. No. 3,930,311 are stamped from sheet metal and include a holding notch therein having the same width as the slot of the plastic bracket body. The reinforcement member is inserted in the bracket body such that the holding notch is flush with the surfaces of the slot in the bracket body. An arch wire placed in the slot will thus be in contact with the plastic surfaces of the slot as in unreinforced plastic brackets. Such contact between the arch wire and the plastic surfaces may make movement of the bracket relative to the arch wire difficult and lengthen the time of orthodontic treatment. Another problem in U.S. Pat. Nos. 4,299,569 and 4,302,532 is easy removal of metal reinforcements during clinical application.

The coefficient of static friction between arch wires made from stainless steel or a nickel-titanium alloy and metal surfaces is about 0.15 to 0.2. By contrast, the coefficient of friction between the arch wire and plastic surfaces is about 0.4 to 0.6. Accordingly, smooth movement of the bracket with respect to an arch wire is difficult to achieve in known reinforced plastic brackets.

Furthermore, if known reinforced plastic brackets are to be provided with torque-angulation, a large variety of metal reinforcement members will be needed to provide brackets adapted for use with various types of teeth, orthodontist techniques and individual patient cases as shown in FIGS. 11 and 12 of U.S. Pat. No. 3,930,311. The costs for making such a variety of reinforcement members are high because many metal molds and stamping plates are required.

Moreover, in known reinforced plastic brackets, the inserted metal reinforcement member is designed to be substantially large to reinforce the slot and wing portions of the bracket. The reinforcement member shown in FIGS. 16 and 17 of U.S. Pat. No. 3,930,311 includes a wide base with a plurality of holes. The large size of the reinforcement member may however make the plastic bracket less aesthetically appealing.

SUMMARY OF THE INVENTION

The present invention is directed at overcoming various problems of known reinforced plastic brackets. In accordance with the invention, a reinforcement member having a holding notch is embedded in a plastic bracket body. The width of the holding notch is less than the width of the slot formed in the bracket body. The holding notch is located in the slot such that an arch wire can be engaged by the holding notch to substantially avoid contact with the surfaces of the slot.

The reinforcement member is designed to be used in brackets with or without torque-angulation. If the reinforcement member is made of a metallic material, it is preferably coated or plated to give it a whiter appearance.

In accordance with another embodiment of the invention, the base of a bracket including a filler material therein may be irradiated to create a base surface that can be more securely bonded to a tooth. In accordance with a further embodiment of the invention, an inorganic phase may be formed on the base surface of a bracket, and a silane coupling agent may be applied on the inorganic phase for more securely bonding the bracket to a tooth.

Brackets in accordance with the present invention differ from known reinforced brackets in that the holding notch of the reinforcement member forms the effective arch wire slot of the bracket. The holding notch of the reinforcement member has a smaller width than the slot of the bracket body such that the notch projects inside the slot. Accordingly, an arch wire can be engaged by the projected holding notch such that contact between the arch wire and the plastic slot surface of the bracket body is substantially avoided. The durability of the bracket is thus increased, while allowing a bracket affixed to a tooth to be smoothly moved along the arch wire.

BRIEF DESCRIPTION OF DRAWINGS

FIGS. 11–14 are front, side, rear and bottom views, respectively, of a bracket in accordance with a further embodiment of the invention.

DETAILED DESCRIPTION

Figure 1:
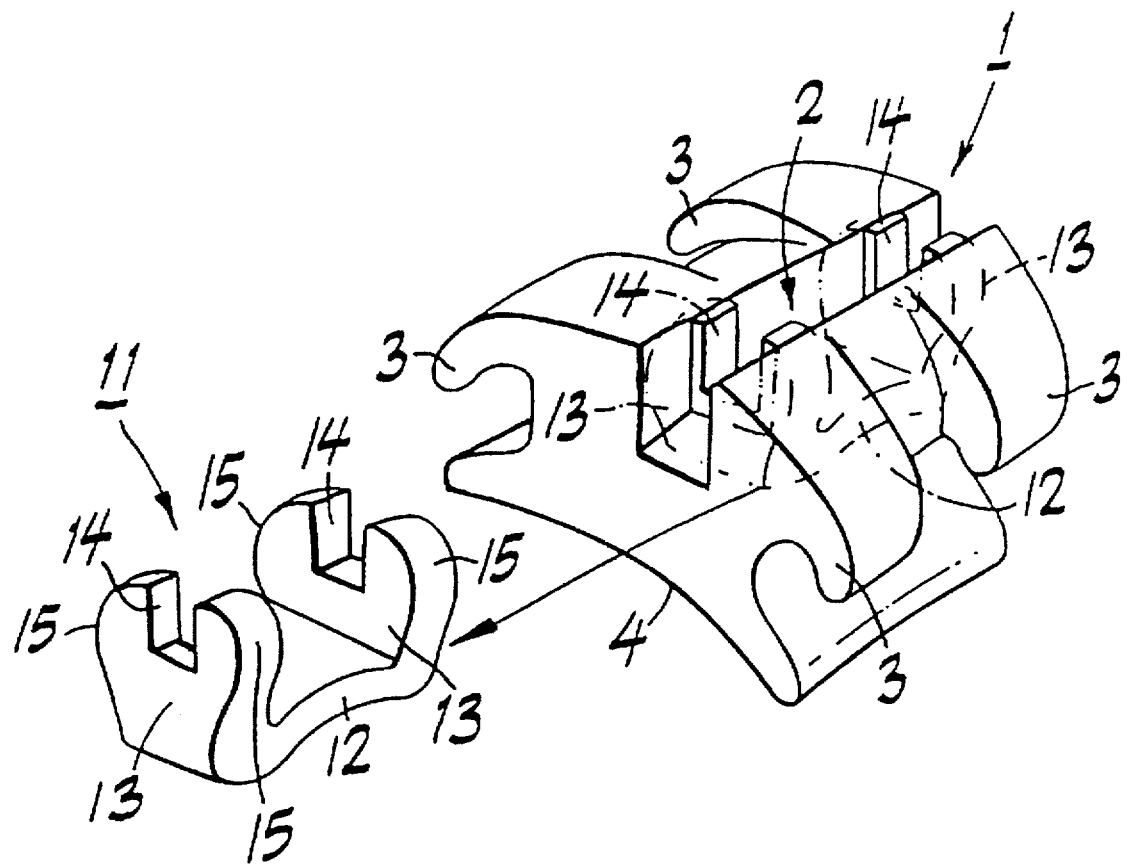
FIG. 1 is a perspective view of a bracket in accordance with a first embodiment of the invention illustrating the bracket body and the reinforcement member.

A bracket in accordance with a first embodiment of the invention comprises a plastic bracket body 1 and a metal reinforcement member 11 embedded in the bracket body as shown in FIG. 1. The bracket is a twin type bracket including a U-section slot 2 extending in mesial-distal direction and two twin-wings 3 at the sides of the bracket to allow ligation of an arch wire to the bracket.

Figure 2:
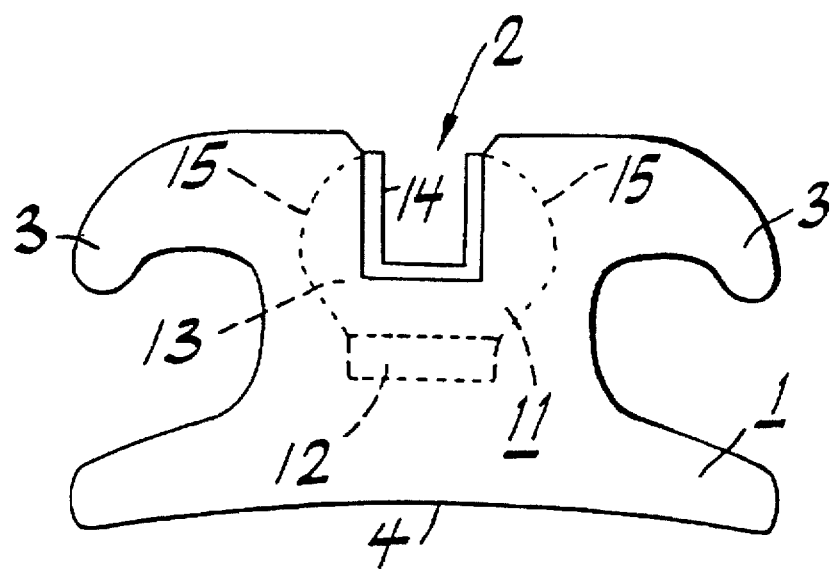
FIG. 2 is side view of the FIG. 1 bracket.
Figure 3:
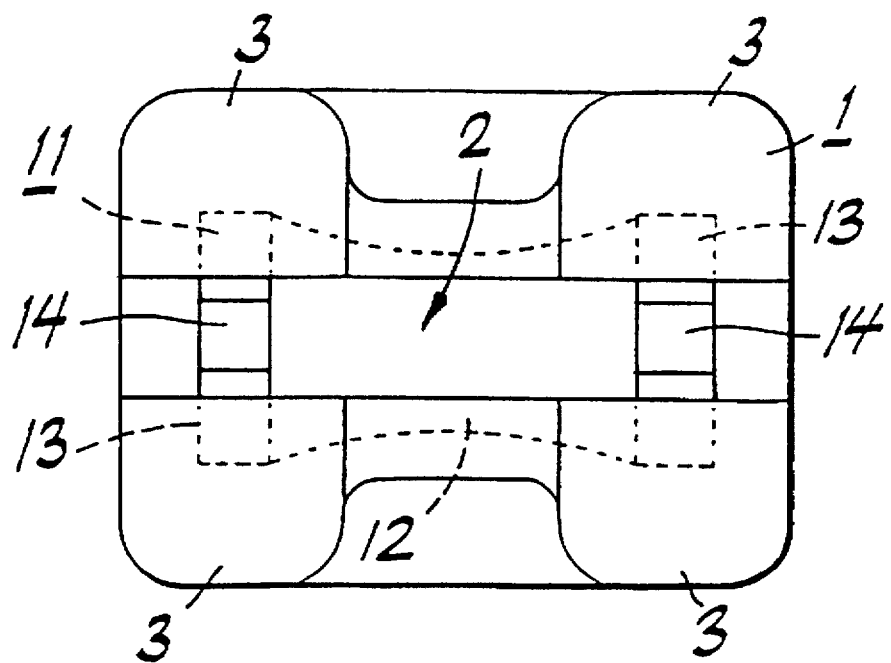
FIG. 3 is a front view of the FIG. 1 bracket.

The metal reinforcement member 11 is provided to increase the durability of the bracket body 1. The reinforcement member 11 includes an elongated base 12 and a pair of upward projections or risers 13 on opposite sides of base 12 giving the reinforcement member a U-shape. A holding notch 14 having a width smaller than that of the slot 2 of the bracket body is provided in the upper center portion of each riser 13. The sides of each riser 13 form a circular arc 15. When the metal reinforcement member 11 is embedded in the bracket body 1, the holding notches 14 of the metal reinforcement member 11 project through the plastic slot surfaces 2 as shown in FIGS. 1–3.

In particular, the holding notches in the metal reinforcement member 11 are designed to be spaced about 0.05 to 0.2 mm away from both sides and the bottom of the slot of the bracket such that the arch wire can be engaged and held substantially only by the holding notches 14 of metal reinforcement member 11.

The metal reinforcement member 11 may be formed by casting, metal injection molding, stamping or machining and should have a Vickers hardness greater than 200. Particularly, if the reinforcement member is stamped, the workpiece should be shaved to remove burrs. Also any sagging on the stamped surfaces should be corrected. The risers 13 of the metal reinforcement member 11 forming the holding notch 14 should be sufficiently thick to support the arch wire without deformation. The thickness of the risers in mesial-distal direction is preferably 0.3 to 0.5 mm. Although the dimensions of the reinforcement member can be varied, a total of six varieties including two series of 0.018-inch and 0.022-inch thickness, a reinforcement member with a narrow span between holding notches for the lower anterior teeth, a wide span for the upper central teeth and the upper cuspids, and a medium span for other teeth, should be sufficient to meet commercial requirements.

The bracket body may be transparent comprising a polycarbonate or acrylic resin material or semi-transparent including filler material. In either case, the appearance of bracket can be improved by plating or coating the metal reinforcement member 11 to give it a whiter appearance.

After being stamped, the reinforcement member may be heat treated and tumbled to roughen its outer surfaces. It can then be silver plated.

Adhesion of the reinforcement member to the bracket body was found to be satisfactory when the coating or plating on the reinforcement member was 3–7 µm thick and the surface was sufficiently rough. Experimental results have found the roughness of the reinforcement surface to be as high as 5 to 10 µm after plating, compared with a 1 to 2 µm roughness of a finished surface of a cold rolled steel plate before plating. If increased adhesive strength is required, a chemical coupling treatment may be applied to the plated or coated surface.

Figure 4A:
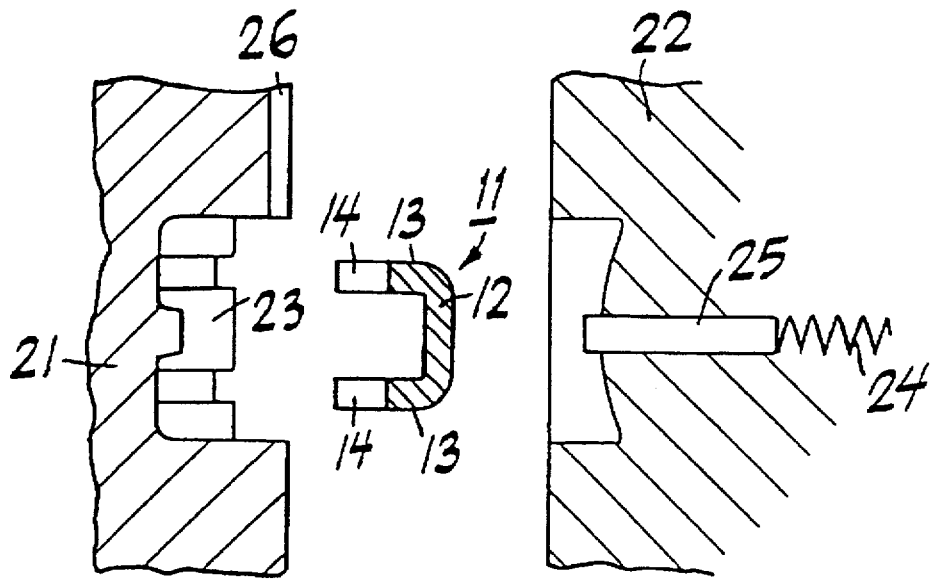
FIGS. 4(A) and 4(B) are cross-section views of a mold apparatus illustrating different steps in the fabrication of the bracket.
Figure 4B:
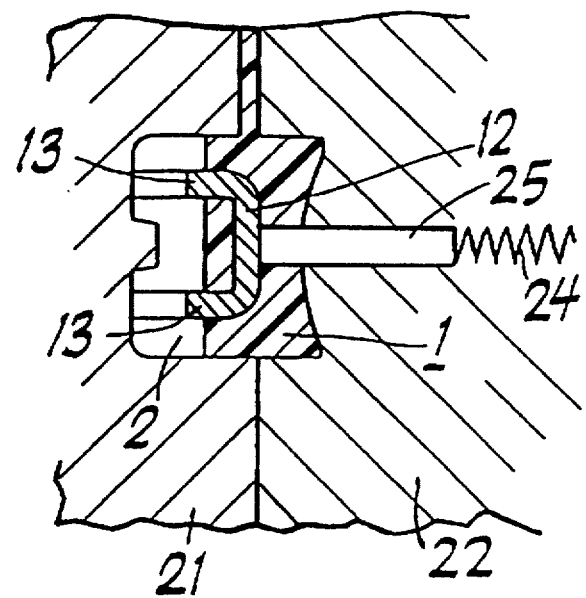

The process of forming a bracket 1 with a metal reinforcement member 11 embedded therein is illustrated in FIG. 4. A slot forming projection 23 is movably located in a fixed mold portion 21 of a mold. The metal reinforcement member 11 is positioned and held on the slot forming projection as shown in FIG. 4A. The metal reinforcement member 11 can be either manually or automatically set on the slot projection 23 while the mold is in an open position. Next, a movable mold portion 22 of the mold is moved against the fixed mold 21 to close the mold. The base 12 of the metal reinforcement member 11 is held against the projection 23 by a press pin 25 in the movable mold 22 under force of a spring 24. Melted resin material is then introduced in the mold cavity through a gate 26. The resin material is maintained and cooled in the mold under predetermined time and pressure conditions, producing a reinforced plastic bracket like that shown in FIGS. 2 and 3 with a metal reinforcement member 11 therein.

Unlike the prior art, in accordance with the present invention, the metal reinforcement member 11 is not flush with the surfaces of the slot 2 of the bracket body. Instead, with the sides of the holding notches 14 of the reinforcement member project a distance of about 0.05 to 0.2 mm into the slot 2 of the bracket body 1.

An arch wire can thus be supported in an effective arch wire slot formed by the projected twin holding notches 14 to substantially avoid contact with the resin slot surface of the bracket body 1. The bracket affixed to a patient's tooth can thus be more easily moved along the arch wire, allowing more effective orthodontic treatment.

Figure 5:
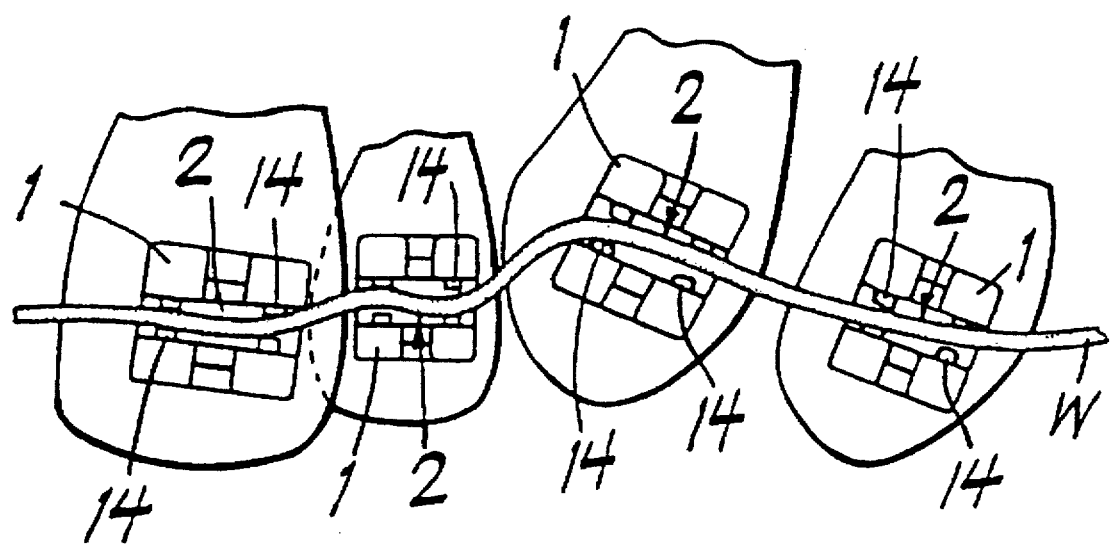
FIG. 5 is a front view of a set of teeth on which brackets have been mounted holding an arch wire.

Brackets in accordance with the invention are particularly suitable for tooth extraction cases that require significant movement of cuspids or bicuspids. The brackets are particularly suitable in cases where anterior teeth are crowded as shown in FIG. 5. Because the pair of holding grooves 14 in each bracket form the arch wire slot of the bracket, the effective distance between brackets on adjacent teeth is increased. In addition there is a distance of about 0.05 to 0.2 mm between each of the two holding notches and the surfaces defining the slot in the bracket body. Accordingly, three-dimensional arch wire control is possible from the initial stages of treatment as a highly rigid arch wire (W) or an angular arch wire can be bent and used with the brackets to accelerate orthodontic treatment.

Brackets in accordance with the first embodiment were tested against prior art plastic brackets. A rectangular arch wire having cross-sectional dimensions of 0.018-inch by 0.025-inch was connected by ligating rings to a bracket in accordance with the invention and to a prior art plastic bracket. The arch wire was then pulled at the speed of 0.5 mm/min. The measured load applied by the arch wire on the bracket in accordance with the invention was 45 to 50 grams. By contrast, the load on the bracket made of pure plastic was 85 to 90 grams.

The reinforcement member may comprise a precipitation hardenable steel such as SUS630 stainless steel. While the reinforcement member 11 in accordance with the invention preferably comprises a metallic material, other materials like plastics and ceramics may be suitable if the hardness and the coefficient of static friction of these materials is satisfactory.

Figure 6:
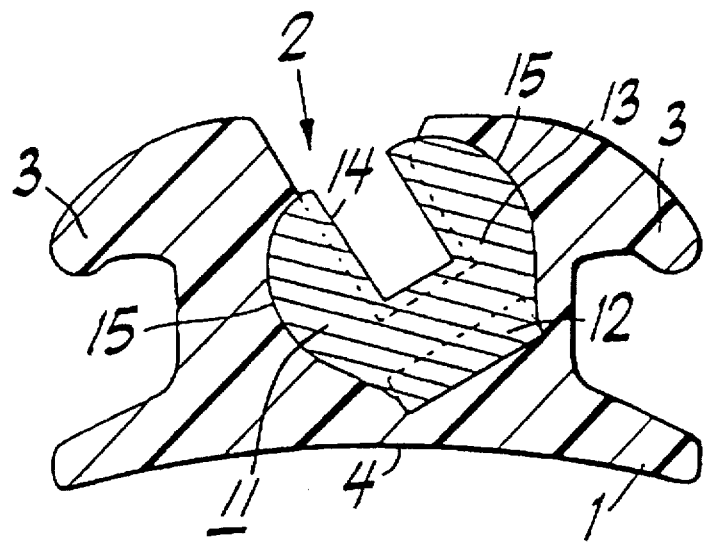
FIG. 6 is a side cross-section view of a bracket in accordance with the invention illustrating the orientation of a metal reinforcement member therein to provide torque and/or angulation.

The metal reinforcement member 11 described above can also be used in a bracket providing torque and/or angulation as shown in FIG. 6. The bracket shown in FIG. 6 can be formed by simply re-orienting the slot forming projection 23 in the mold as needed and inserting the reinforcing member 11 thereon. It is therefore unnecessary to have a variety of metal reinforcement members 11 for use in brackets for particular teeth, orthodontist techniques or individual patient cases. Brackets in accordance with the invention can therefore be economically produced.

The outer edges of each riser 13 of the metal reinforcement member 11 have a circular arc shape 15. Accordingly, the metal reinforcement member 11 can be oriented in the bracket 1 at various angles, without interference from the edges of the risers 13. A reinforcement member 11 of the same design can thus be used in brackets having varying degrees of torque angulation. Mold costs for making reinforcement members can thus be significantly reduced.

A plastic bracket in accordance with a second embodiment of the invention is similar in structure to the first embodiment described above, but is characterized by an improvement to the base surface 4 of the bracket 1.

Plastic brackets are normally affixed to a patient's teeth with the use of dental bonding agents like Bis-GMA series composite resin, light cure type Bis-GMA series resin, 4-META adhesive resin and others. The application of a primer on the bonding surface of the bracket is desirable for obtaining proper adhesion to the teeth. Application of a primer however increases the number of steps and lengthens the time for affixing the brackets to the teeth. Therefore, a bracket made of plastic that can be securely bonded to teeth using a conventional bonding agent without use of a primer is desirable.

The bracket in accordance with the second embodiment was formed from a resin or a polycarbonate material filled with a filler material. The base surface 4 of the bracket was irradiated with an excimer laser heat ray up to a depth of 0.1 to 0.3 mm. The resulting base surface structure provided an anchoring effect for affixing the bracket to a tooth surface.

Figure 8:
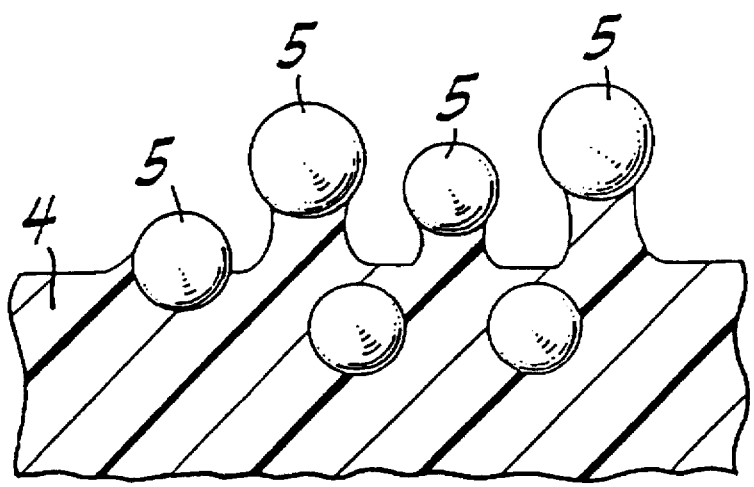
FIG. 8 is an enlarged cross-section view of a portion of the base surface of a bracket in accordance with a second embodiment of the invention.
Figure 7A:
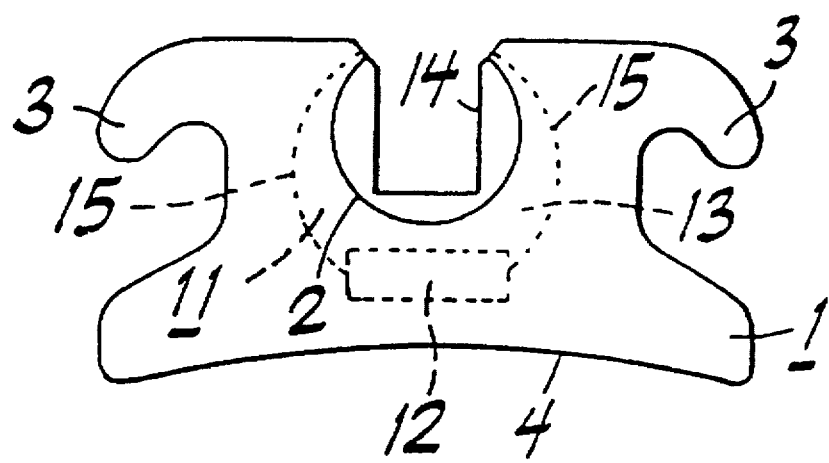
FIG. 7(A) is a side view of a bracket in accordance with the invention with a reinforcement member therein.
Figure 7B:
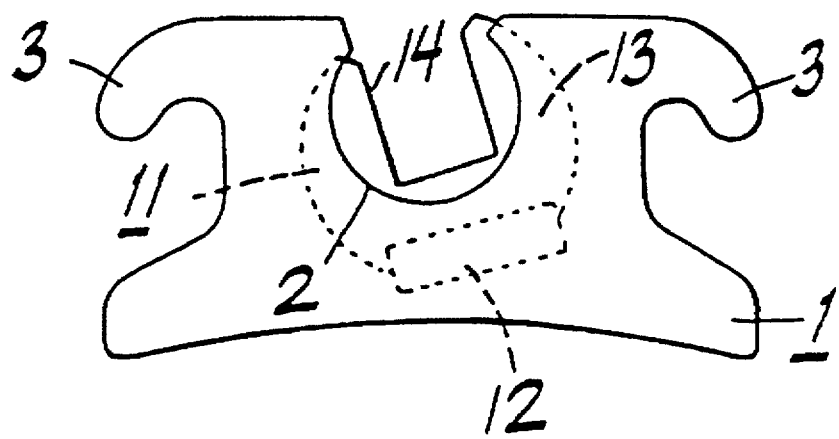
FIG. 7(B) is a side view of the bracket with the reinforcement member mounted therein for providing torque and/or angulation.

In particular, glass beads of 10 to 30 µm diameter were used as the filler 5. A polycarbonate bracket base filled by volume with 15% glass beads was irradiated by an excimer laser at an energy density of 1.5 J/cm$^2$ per pulse at a processing speed of 0.2 µm for about 5 seconds at 1000 pulse up to a depth of 0.2 mm. Using a microscope, it was found that glass beads were present above the polycarbonate material as shown in FIG. 8 to provide an anchoring structure on the base surface.

The bracket body may also comprise polycarbonate material filled by weight with 30% silica.

Bracket 1 in accordance with the second embodiment were affixed to teeth using a Bis-GMA series composite resin. A shear bond strength of 10 to 15 kg was measured for the brackets or 100 to 150 kg/cm$^2$ per unit area, which meets the 100 kg/cm$^2$ bond strength requirement for usual orthodontic treatment.

While the filler material 5 comprised glass beads in the above example, other inorganic or organic substances can be used. The filler 5 is also not limited to solid spherical matter; plate, fibrous, bar materials, hollow spheres, and other matter may also be used.

Figure 9:
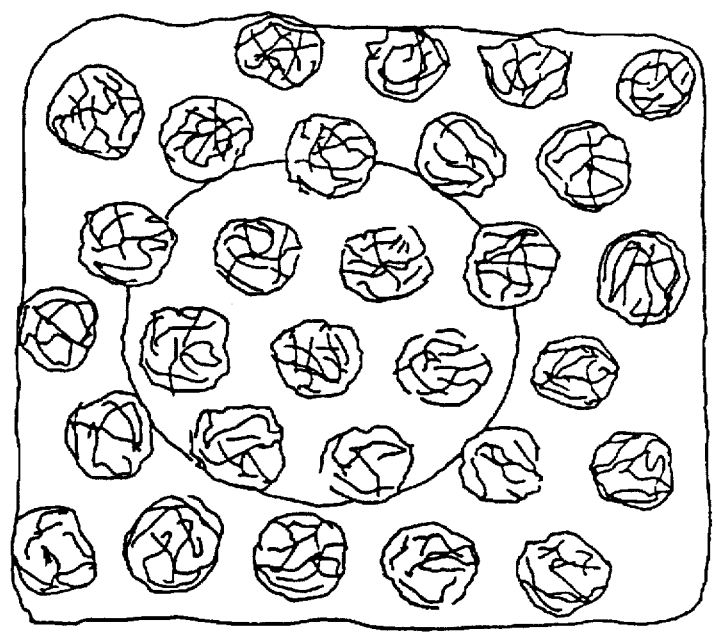
FIG. 9 is a photograph illustrating an enlarged top view of the base surface of the bracket in accordance with another embodiment of the invention.
Figure 10:
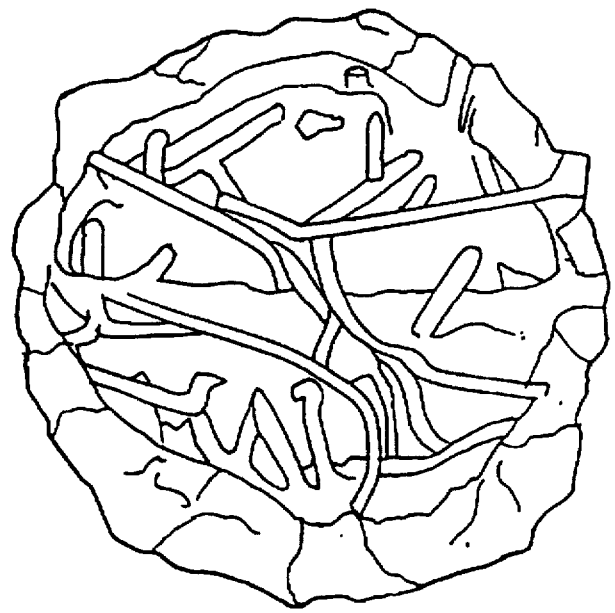
FIG. 10 is a photograph illustrating a magnified view of a portion of the base surface shown in FIG. 9.

FIGS. 9 and 10 are enlarged photographs of the base surface 4 of a bracket including fibrous filler material therein in accordance with the invention. FIG. 9 is a view of the entire base surface, and FIG. 10 is a magnified view of a portion of the base surface shown in FIG. 9.

The bracket of FIGS. 9 and 10 comprises polycarbonate plastic with 30% glass fiber filler. The base surface was flashed by an excimer laser to a melting depth of 0.1 mm. Masking was used such that selective portions of the base surface were flashed. The resulting base surface as shown in FIGS. 9 and 10 includes exposed glass fibrous material that provides anchoring means for securely affixing and mechanically locking the base surface on a tooth (not shown).

The filler material in the bracket body may be exposed at the base surface by application of a laser thereon or by other suitable means, including application of a solvent on the base surface.

In a bracket made in accordance with a third embodiment of the invention, the base surface 4 of the bracket 1 does not include a filler 5 as in the previously described second embodiment. Inorganic aluminum oxide powder is applied on the base surface 4 by a plasma injection to form an inorganic phase having a thickness of 0.1 mm. A silane coupling agent is then applied on the inorganic phase.

The bracket 1 in accordance with the third embodiment was measured to have a shear strength of 15 to 20 kg on the base surface 4, which has an area of about 10 mm$^2$. The adhesive strength of the base surface 4 is about 150–200 kg/cm$^2$ per unit area. The inorganic powder applied by plasma injection was about 10 to 30 µm in diameter. A color of the inorganic phase is white and therefore does not adversely affect the appearance of the bracket.

The brackets previously described were twin type brackets. The present invention is however not limited to twin type brackets and is also applicable to single type brackets. A metal reinforcement member used in a single type bracket would include a holding notch as previously described and be shaped to conform to a single wing design.

In accordance with another embodiment of the invention, the base of a bracket including a filler material may be irradiated to form a base surface that can be securely bonded to a tooth. In accordance with a further embodiment of the invention, an inorganic phase may be formed on the base surface of the bracket, and a silane coupling agent may be applied on the inorganic phase for securely affixing the bracket to a tooth. Accordingly, a bracket in accordance with the invention can be securely bonded to a tooth without need for a wide conventional base plate that may adversely affect the appearance of the bracket.

A bracket 30 shown in FIGS. 11–14 is marked in accordance with a further embodiment of the invention. FIG. 13 is the rear view of the bracket 30 illustrating the back of the base 32 of the bracket 30, that is, the lingual surface 34 of the bracket, which is adapted to be affixed to a tooth (not shown). Identification characters 35 (shown for example as "U3L" in the drawing) are molded in recessed portions 36 of the lingual surface 34 of the bracket 30. An important advantage of locating the identification characters 35 on the lingual surface 34 is that after cement or other bonding material is applied to the lingual surface 34 to bond the bracket 30 to the tooth, the reference characters should not be noticeable. If the reference characters are molded on the opposite labial surface 37 of the bracket 30, the projections or indentations defining the marking may reflect light and adversely affect the aesthetic appearance of the bracket 30.

FIG. 11 illustrates a suitable marking of the labial surface 37 of the bracket 30, which acts as a positioning guide allowing the practitioner to properly align the bracket on a tooth during installment without use of a height gauge. In the drawing, a pair of crossed lines 39 are shown as an example of such a marking. The marking is made with an ink that is non-toxic and soluble such that when placed in an oral environment, it quickly dissolves and is removed from the labial surface or it can be easily brushed off with a tooth brush during usual brushing. The marking will thus not affect the appearance of the bracket when in use.

The lines 39 of the marking each comprise a plurality of dots that can be ink jet printed on the bracket. A very small amount of ink is needed for the marking (about $8.3 \times 10^{-7}$ cc per dot). The ink is soluble in water, alcohol or MEK. The ink may have one of several colors, including for example, black, yellow, red and blue.

In summary, a bracket in accordance with the invention allows an arch wire to be held in an effective arch wire slot formed by a holding notch of a reinforcement member embedded in the bracket body. Accordingly, the arch wire substantially avoids contact the resin slot surface. The reinforcement member thus increases the durability of the plastic bracket while allowing the bracket to be smoothly moved along an arch wire when secured to a tooth.

A reinforcement member of the same design can be used in brackets with or without torque and/or angulation. It is therefore unnecessary to have a variety of reinforcement members for use in different brackets to meet the needs of different types of teeth, orthodontist techniques, and individual patient cases as previously required.

Further, the bracket of this invention may be enhanced with filler materials on the base for enhancing bonding to the tooth. Also, the bracket may be provided with identification and alignment characters and markings that facilitate its use by the practitioner.

We claim:

1. An orthodontic bracket, comprising a plastic bracket body including surfaces defining an arch wire slot extending along a mesial-distal axis of the bracket body, said bracket body also including a base having a surface affixable to a tooth, wherein said base surface includes mechanical anchoring means to improve bonding of the bracket to the tooth, said anchoring means comprising filler material extending outwardly from said base surface.

2. The bracket of claim 1, wherein said filler material comprises glass beads.

3. The bracket of claim 1, wherein said filler material comprises fibrous material.

4. The bracket of claim 1 wherein said bracket body comprises polycarbonate material.

5. A method of forming an orthodontic bracket, comprising the steps of:

forming a bracket body from a plastic material including a glass filler material therein, said bracket body including a base surface adapted to be affixed to a tooth; and treating said base surface to expose a portion of said glass filler material at said base surface to form mechanical anchoring means to facilitate secure attachment of said bracket to the tooth.

6. The method of claim 5 wherein said glass filler material comprises glass beads.

7. The method of claim 5, wherein said glass filler material comprises glass fibers.

8. The method of claim 5, wherein said step of treating said base surface comprises applying an excimer laser on said base surface.

9. The method of claim 8, wherein said step of applying an excimer laser comprises irradiating said base surface up to a depth of about 0.1 mm of said base surface.

10. The method of claim 5, wherein said step of treating said base surface comprises applying a solvent on said base surface.

11. An orthodontic bracket, comprising a bracket body including surfaces defining a slot extending substantially along a mesial-distal axis of the bracket body for receiving an arch wire, wherein said bracket body comprises glass-filled plastic material, and wherein said bracket body includes a base surface treated to expose portions of the glass material in the bracket body to provide mechanical anchoring means for securely affixing the bracket to a tooth.

12. The orthodontic bracket of claim 11, wherein the bracket body comprises polycarbonate plastic material filled by weight with 30% silica.

* * * * *